United States Patent [19]

Matsubara et al.

[11] Patent Number: 5,524,705
[45] Date of Patent: * Jun. 11, 1996

[54] METHOD FOR CASTING OXIDIZATION-ACTIVE METAL UNDER OXYGEN-FREE CONDITIONS

[75] Inventors: Norio Matsubara; Shouichirou Miyazaki, both of Kitakyushu, Japan

[73] Assignee: U-WA Tech Corporation, Tokyo, Japan

[ * ] Notice: The portion of the term of this patent subsequent to Apr. 8, 2014, has been disclaimed.

[21] Appl. No.: 211,593

[22] PCT Filed: Aug. 9, 1993

[86] PCT No.: PCT/JP93/01116

§ 371 Date: Apr. 8, 1994

§ 102(e) Date: Apr. 8, 1994

[87] PCT Pub. No.: WO94/04299

PCT Pub. Date: Mar. 3, 1994

[30] Foreign Application Priority Data

Aug. 11, 1992 [JP] Japan ................. 4-214286

[51] Int. Cl.$^6$ .................. B22D 27/13; B22D 27/15
[52] U.S. Cl. .................. 164/495; 164/61; 164/68.1
[58] Field of Search .................. 164/492, 493, 164/494, 495, 62, 61, 66.1, 68.1, 512, 513, 514, 256, 258

[56] References Cited

U.S. PATENT DOCUMENTS

| | | | |
|---|---|---|---|
| 4,762,165 | 8/1988 | Ogino et al. | 164/61 |
| 5,168,917 | 12/1992 | Okuda et al. | 164/495 |

FOREIGN PATENT DOCUMENTS

| | | |
|---|---|---|
| 56-1981 | 5/1980 | Japan . |
| 62-89559 | 4/1987 | Japan . |
| 1-180774 | 7/1989 | Japan . |

*Primary Examiner*—Kuang Y. Lin
*Attorney, Agent, or Firm*—Wenderoth, Lind & Ponack

[57] ABSTRACT

A method for casting oxidization-active metal under oxygen-free conditions wherein air is discharged from a melting chamber and a casting chamber while maintaining the condition of the melting chamber pressure $P_R >$ the casting chamber pressure $P_C$ and dry compressed inert gas is then introduced into the melting chamber, directionality is imparted to the atmosphere gas of the melting chamber under the condition of $P_R > P_C$ for replacing and discharging the atmosphere in a mold of the casting chamber with inert gas and establishing a non-oxidizing atmosphere in the melting chamber and the casting chamber, and precision casting is thereafter conducted by melting a fusible casting material and pouring it into the mold in the casting chamber.

2 Claims, 4 Drawing Sheets

① PRESSURE DIFFERENTIAL (②-③)

② MELTING CHAMBER PRESSURE

③ CASTING CHAMBER PRESSURE

METHOD FOR CASTING OXIDIZATION-ACTIVE METAL UNDER OXYGEN-FREE CONDITIONS

TECHNICAL FIELD

This invention relates to a method for casting oxidization-active metal under oxygen-free conditions.

BACKGROUND ART

Oxidization-active metals such as pure titanium and titanium alloy materials consisting mainly of titanium exhibit high heat resistance, excel in such mechanical properties as toughness and wear resistance, and being highly biocompatible, do not harm living organisms in which they are embedded. They therefore have the potential for extensive utility not only in industry but also in dental prosthetics, plastic surgery and other such surgical and medical fields.

However, since titanium materials are very active and are therefore exceedingly difficult to work, it has only been possible to process them in vacuo using special equipment and techniques. Because of this, it has not been possible to fabricate dentures and other complex, intricate articles from titanium.

JP-B 56-1981, for example, discloses that oxidization and other qualitative changes in a metal are prevented by maintaining an inert gas atmosphere in the melting chamber and the casting chamber from before the metal is melted until after it is cast. JP-B 56-1981 further discloses that the running of the metal is improved by causing the inert gas to pass under a differential pressure from the melting chamber through a gap passage, a passage hole, the sprue of the mold and the shaped cavity into the casting chamber so that at the time the metal is poured into the mold after being completely melted the molten metal flows smoothly into the deep regions of the shaped cavity of the mold as entrained by the inert gas flow.

The present invention proposes a method for non-oxidize casting of oxidization-active metal in which the absolute amount of oxygen is reduced to an ultra-low level by drying the mold.

DISCLOSURE OF THE INVENTION

The present invention is directed to a method for casting oxidization-active metal under oxygen-free conditions comprising a step of discharging air from a melting chamber and a casting chamber while maintaining the condition of the melting chamber pressure $P_R$> the casting chamber pressure $P_C$, i.e., the compressed gas pressure, and then introducing dry compressed inert gas into the melting chamber, a step of imparting directionality to the atmosphere gas of the melting chamber under the condition of $P_R$> $P_C$ for replacing the atmosphere in a mold of the casting chamber with inert gas and establishing a non-oxidizing atmosphere in the melting chamber and the casting chamber, and a step of precision casting conducted by thereafter melting a fusible casting material and pouring it into the mold in the casting chamber, wherein the mold is dried by introducing dry compressed inert gas into the melting chamber while maintaining the condition of $P_1$>$P_2$.

As the means for evapotranspiring and discharging oxygen, hydrogen and the like from the interior of the mold to the exterior so as to strongly suppress oxygen in the mold, the present invention introduces inert gas into the melting chamber 8 under high pressure after the air pressure in the casting chamber 9 has reached a prescribed degree of vacuum, thus establishing a high differential pressure (melting chamber at positive pressure higher than atmospheric pressure →casting chamber at pressure lower than atmospheric pressure and in a vacuum, thereby imparting the inert gas with directionality for passing, evapotranspiring and drying the mold moisture content.

Further, after evapotranspiring and drying the moisture content in the mold (the first purging), the same process is repeated multiple (two or more) times for controlling the interior of the melting chamber to an anoxic atmosphere by suppressing the absolute amount and concentration of oxygen therein to an ultra-low level, thereby establishing a state enabling selection of an appropriate pressure condition for arc discharge. This enables casting which is capable of forming ultra-fine features free of blowholes produced by reaction with oxygen.

BEST MODE FOR CARRYING OUT THE INVENTION

The invention will hereinafter be explained with reference to the drawings.

Figure 1:
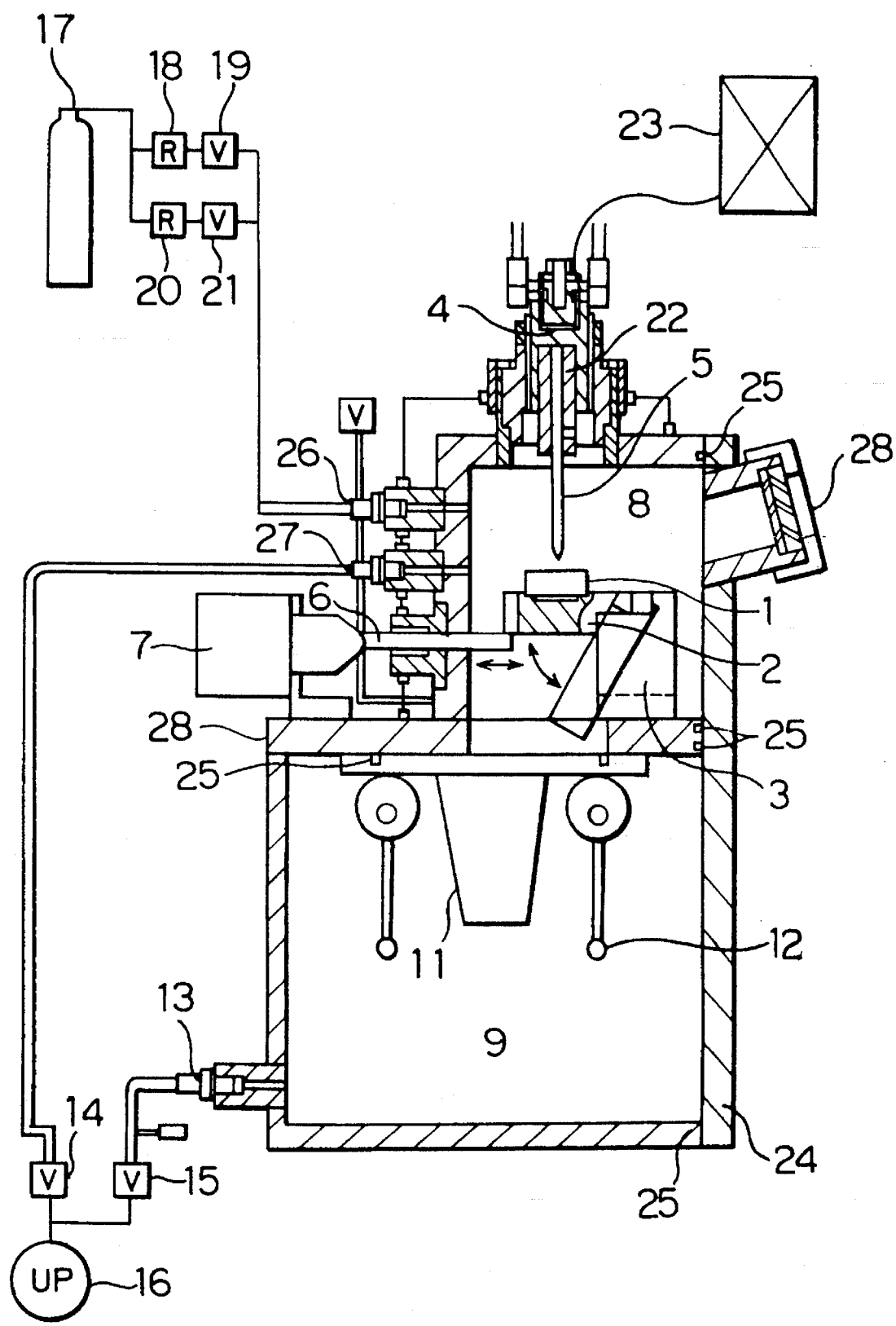
FIG. 1 is an overall explanatory view of the present invention.

In FIG. 1, a door 24 of a melting chamber 8 is opened and a fusible casting material 1 is placed on a melting plate 2.

On the other hand, a mold (not shown) is placed in a mold holder 11 of a casting chamber 9, is positioned in the mold holder so as to align with the center of sprue, and the mold is fixed with a mold clamp 12 thereby selecting the optimum position for casting.

Next, a vacuum pump 16 is operated and a solenoid valve 15 is opened for discharging air from the casting chamber 9 through a connection port 13. After the air pressure of the casting chamber 9 has reached a prescribed degree of vacuum, a solenoid valve 14 is opened for discharging air from the melting chamber 8 through a connection port 27. After a prescribed degree of vacuum has been attained, the solenoid valves 15, 14 are closed and the vacuum pump 16 is stopped.

Since the air discharge is conducted while maintaining the condition $P_R$> $P_C$, air does not flow from the casting chamber 9 into the melting chamber 8.

Next, a solenoid valve 21 is opened to supply inert gas into the melting chamber 8 and the casting chamber 9 at a prescribed pressure controlled by a pressure reduction valve 20 connected with a gas cylinder 17. The solenoid valve 21 is closed after compressed dry inert gas introduced into the melting chamber 8 has first been supplied to the mold for a prescribed period of time. The mold loaded into the casting chamber 9 is a mold block having a shaped cavity. Owing to the condition $P_R$> $P_C$, the moisture in the mold block is evapotranspired by the passage of the inert gas.

At the time of melting the fusible casting material, the inert gas pressures in the melting chamber 8 and the casting chamber 9 are first optimized. The fusible casting material 1 is then melted by an arc discharge established between an electrode 5 and the fusible casting material by passing current from a melter 23 through an electrode holder 4, an electrode positioner 22 and the electrode 5. Reference numeral 3 designates a melting plate holder, 25 seals and 28 a peephole.

The fusible casting material is melted at a temperature 50° C. to 100° C. higher than the melting point of the casting metal. For holding the fusible casting material in this temperature range, the upper portion of the piece of fusible casting material is supplied with a heat source and the conductive melting plate that supports it is constituted of copper or other such material which minimizes the heat conduction and maximizes the heat shielding of the melting chamber etc., thus making it possible to continue arc discharge up to immediately before casting.

After the fusible casting material 1 has been thoroughly heated, a catch rod 6 is operated by a solenoid 7 to allow the crucible 2 to swing down, whereby the upper portion of the heated fusible casting material 1 is poured into the mold in the shortest time. At the time of swinging down, melting plate 2 is forcibly tilted by the compressed gas.

While maintaining the solenoid valve 21 opened, a solenoid valve 19 is opened to supply inert gas from the gas cylinder 17 through a connection port 26 and into the melting chamber 8, high-pressure inert gas set to higher than atmospheric pressure by the pressure reduction valves 18 and 20, whereby a high gas pressure is established in the melting chamber 8 and a high gas pressure acts on the upper portion of the mold.

Since the casting chamber 9 was at low pressure before this supply of the inert gas, a high differential pressure is established relative to the aforesaid low gas pressure, thus enabling ultra-fine feature casting.

In this invention, the design is such that "melting chamber volume $V_1$ < casting chamber volume $V_2$." The reason for this is as follows.

Figure 2:
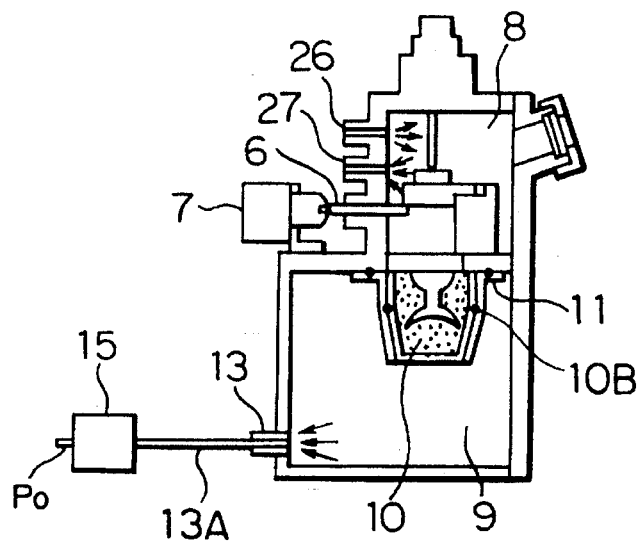
FIG. 2 is an explanatory view of the gas flow in the present invention.

FIG. 2 shows the flow path of the inert gas in the present invention. In this figure, reference numeral 8 designates the melting chamber, 9 the casting chamber, 10 a porous mold, and 15 a solenoid switch valve.

After the atmospheres of melting chamber 8 and casting chamber 9 have been replaced with inert gas, a high differential pressure is established between the melting chamber and the casting chamber prior to pouring of the melt. At this time the inert gas passes from the melting chamber 8→the porous mold 10→the casting chamber 9 through the connection port 13 to be discharged to the outside via the solenoid switch valve 15.

Therefore, for maintaining melting chamber pressure $P_R$>casting chamber pressure $P_C2$, the volume of the melting chamber is determined such that $V_1 \leq T/\alpha \cdot v_0 \cdot 1/P_C$ and the volume of the casting chamber ($V_2$) is determined such that $V_2 = (T \cdot v_R)/\{\alpha(P-P_R)\}$, where

| | | |
|---|---|---|
| $V_1$: | Melting chamber volume | (l) |
| $V_2$: | Casting chamber volume | (l) |
| $v_0$: | Gas influx capability | (l/s) |
| T: | Solidification time | (s) |
| $v_R$: | Gas leakage from mold | (l/s) |
| $P_R$: | Casting chamber pressure at time of arc discharge | (kg/cm² abs) |

-continued

Figure 3A:
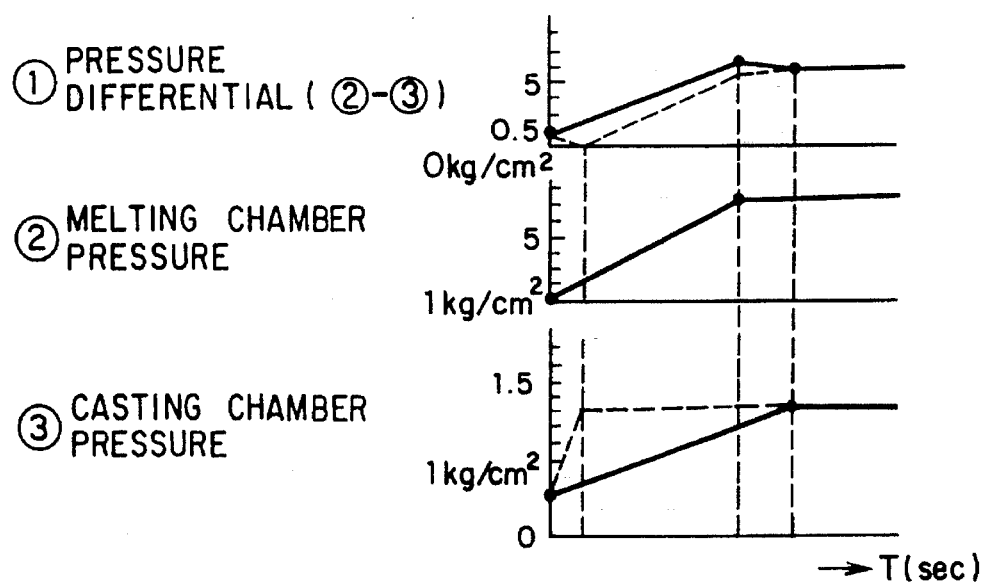
FIGS. 3(a) and (b) are pressure-time diagrams.
Figure 3B:
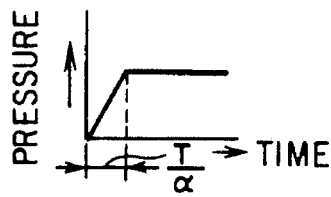

| | | |
|---|---|---|
| $P_C$: | Compressed gas pressure | (kg/cm² abs) |
| P: | Casting chamber atmospheric discharge pressure (P = $P_0 + \Delta P$) | (kg/cm² abs) |
| $\alpha$: | Coefficient which is an experimentally determined numerical value defining the time, relative to the molten metal casting solidification time T, at which the interior of the melting chamber is increased to pressure $P_R$. | |
| T/$\alpha$: | T/2 to 3 = 0.03 T to 0.5 T, as shown in FIG. 3(b). | |

More specifically, it can be considered that the interior of the casting chamber is shut off up to the atmospheric discharge pressure of 1.033 (kg/cm² abs)+$\Delta P$, namely, up to the sum of atmospheric pressure 1.033 (kg/cm² abs) and the pressure loss $\Delta P$ resulting from the internal resistance of the hose piping 13A (FIG. 2) from the casting chamber 9 to the solenoid valve 15. Moreover, since up to the solidification time the pressure of the casting chamber rises owing to the flow of gas from the melting chamber through the mold, the volume of the casting chamber is determined by the foregoing equation and a relationship is established with the pressure rise of the melting chamber.

In other words, assuming the amount of inert gas leakage from the mold and the solidification time to be fixed, if the capacity of the casting chamber is small, the discharge pressure is achieved before the ideal time, the rise in melting chamber pressure and the rise in casting chamber pressure become nearly coincident, the differential pressure between the melting chamber and the casting chamber decreases or become zero (broken line in FIG. 3), and the initial differential pressure, which is most important to be sufficient at the start, is not developed, whereby the castability is degraded.

In the present invention, the mold holder 11 can be fixed on the partition 28 between the melting chamber 8 and the casting chamber 9 by rotating the cam-type mold clamp 12 to clamp it between the partition 28 and the cam side surface, and can thereafter be unclamped by again rotating the mold clamp 12. More specifically, since the mold holder 11 is of a free mold setting type enabling horizontal movement in the X-Y direction, the sprue position of the casting is not restricted. Since it can therefore be set at the shortest distance relative to the casting to enable the high-temperature molten metal to reach the extremities of the casting in a short period of time, it becomes possible to produce large-volume castings.

More specifically, since the center of the falling fusible casting material and the center of the sprue can be aligned by a mold cradle disposed in the casting chamber, fine feature casting can be conducted at the minimum pouring distance.

In addition, since the invention uses a small volume melting chamber for enabling instantaneous pressurization following pouring and a large volume casting chamber for absorbing the compressed fluid leakage from the porous mold and further since, as shown in FIG. 2, the porous mold 11 is tapered and a seal member 10B is attached to the mold holder 11 at a position matched to the tapered portion of the porous mold 10, the porous mold 10 is moved downward and pressed into strong contact with the seal member 10B by the action of the pressure $P_C$ of the compressed gas, thereby enhancing the sealing performance. Since this cell block system sealing method makes it possible to hold the high differential pressure until the cast metal has solidified, the metal can be charged fully to the extremities of an ultra-fine featured casting.

Thus while the prior art methods have not been able to charge reliably down to ultra-fine features without surface oxidization, the present invention is able to melt a low specific gravity metal at a temperature equal to the melting point plus 50° C. to 100° C.

On the other hand, since the melting plate supporting the molten metal is heat insulated from the melting chamber proper, heat conduction is minimized and heat accumulation in the molten metal is maximized.

Moreover, arc discharge is continued up to immediately before pouring so as to heat the molten metal to a high temperature and thus maintain the solidification time.

In addition, by adopting a system structure which shortens the pouring time and the pouring distance as well as a small volume melting chamber which enables instantaneous pressurization following pouring and a large volume casting chamber that permits increase in the fluid leakage pressure, it is possible to establish an ideal high differential pressure.

The heating of the fusible casting material to a high temperature, the shortening of the pouring time and distance, and the high differential pressure make it possible to charge the molten metal down to the ultra-fine feature portions while ensuring a high-quality unoxidized surface.

WORKING EXAMPLE

A cylindrical ingot of JIS Type 2 titanium measuring 12 mm in height and 30 mm in sectional diameter and weighing 40 g was arc-melted with a copper melting plate.

Figure 4A:
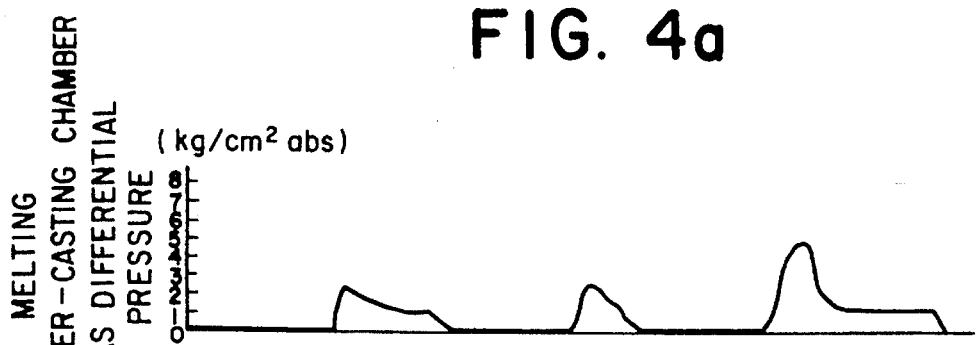
FIGS. 4(a), (b) and (c) are pressure-time diagrams and (d) and (e) are $O_2$ concentration-time diagrams.
Figure 4B:
Figure 4C:
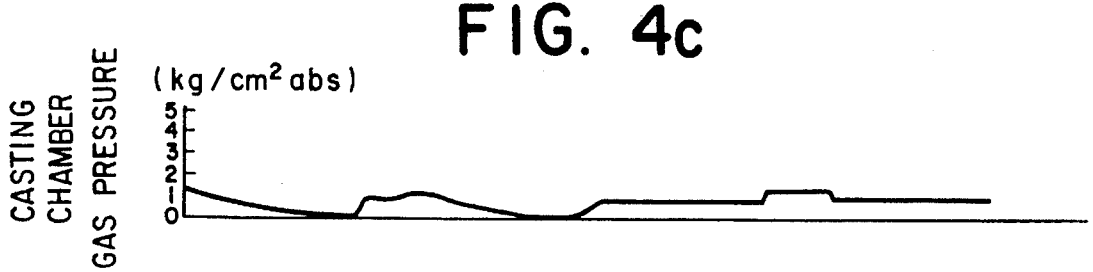

The pressure changes during the melting chamber and casting chamber air discharge step, the purge-drying step, the melting and casting step and the holding step are shown in FIGS. 4(a), (b), (c).

The ingot arc-melting temperature was 1700° C. The amount of overheating at this time was 50° C. to 100° C.

Figure 4D:
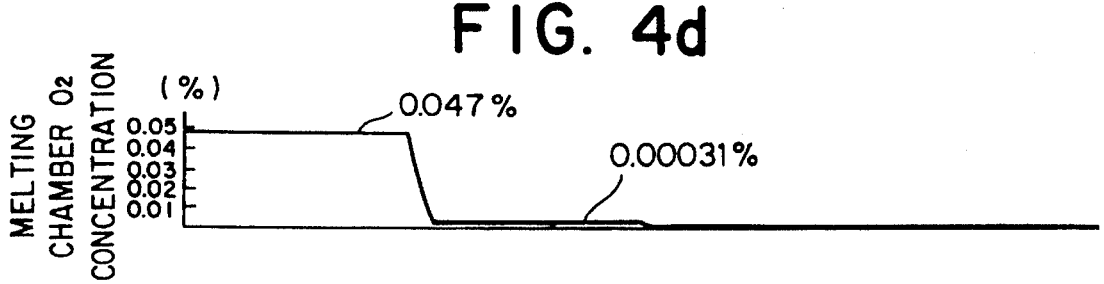
Figure 4E:
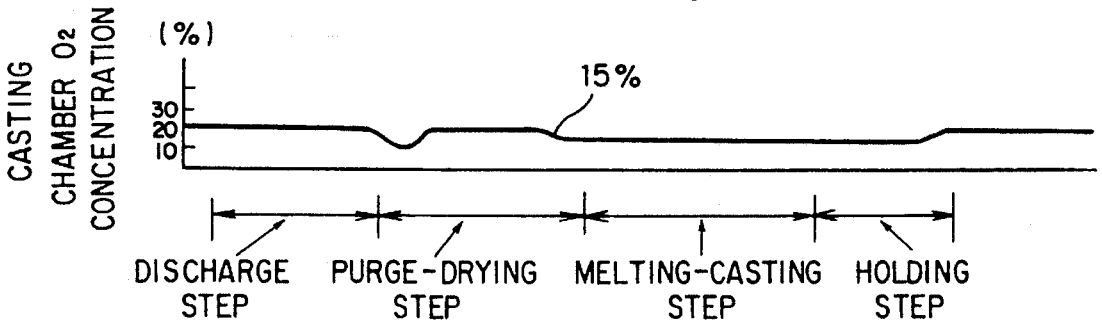

The $O_2$ concentrations of the melting chamber and the casting chamber are shown in FIGS. 4(d), (e). In the present invention, the melting chamber $O_2$ was 0.00031 wt % (melting stage).

Figure 5:
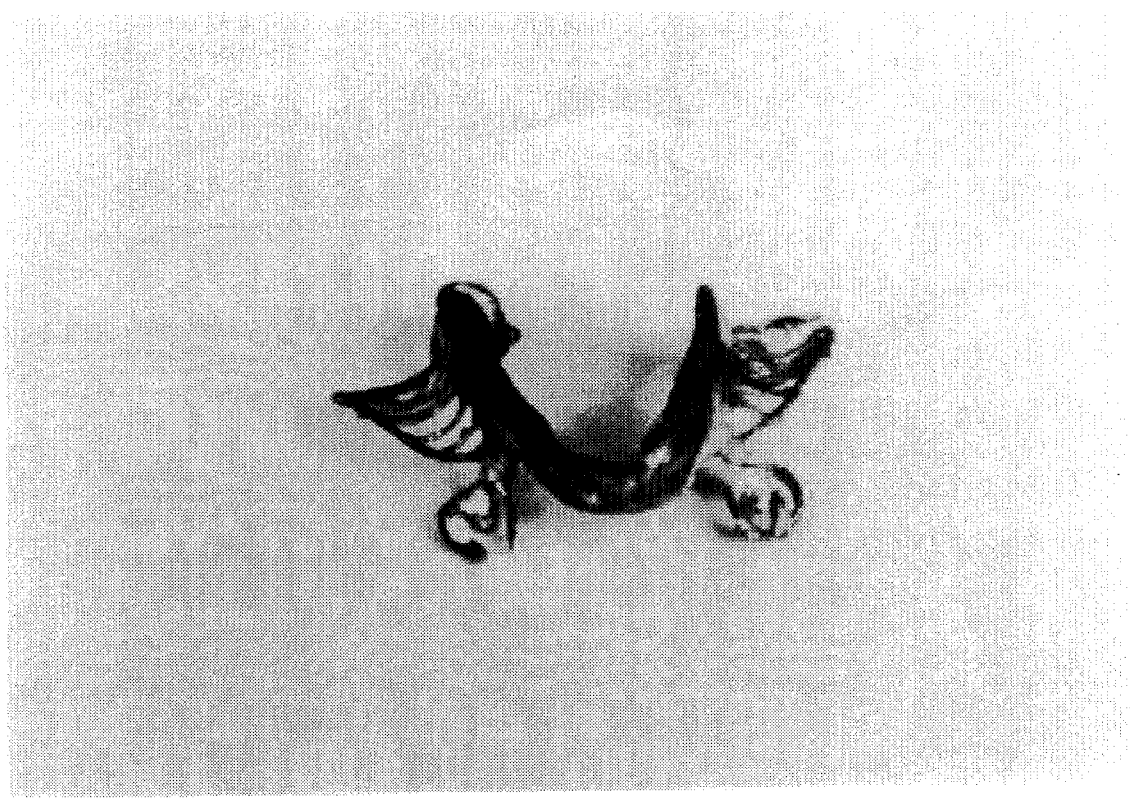
FIG. 5 is a photograph of a casting according to a working example of the present invention.

As shown in FIG. 5, there was as a result obtained a perfect casting free of voids and casted down to the pointed portions at the tips.

INDUSTRIAL APPLICABILITY

In the present invention, since moisture, oxygen and the like are evapotranspired from the mold material by introducing compressed inert gas into the melting chamber such that melting chamber pressure $P_R <$ casting chamber pressure $P_C$, it is possible to avoid degradation and hardening of the casting surface owing to oxidization.

We claim:

1. In an improved method for casting oxidization-active metal under oxygen-free conditions including a step of providing an inert gas supply system including a melting chamber 8 provided with a rotatable crucible 2 and an electrode 5 directed into the crucible 2 and a casting chamber 9 communicating with the melting chamber 8 and having therein a mold holder for setting a mold, the mold having a molding cavity and being charged with a porous embedded material, and an inert gas discharge system for discharging gas from the casting chamber 8, thereby forming an inert gas passage for supplying inert gas to the melting chamber, passing it through the porous mold and discharging it from the casting member, the improvement comprising a step of defining the melting chamber volume $V_1$ and the casting chamber volume $V_2$ such that $V_1 < V_2$, discharging air from the melting chamber and the casting chamber while maintaining the condition of melting chamber pressure $P_R >$ the casting chamber pressure $P_C$ and then introducing dry compressed inert gas into the melting chamber, a step of introducing the atmosphere gas of the melting chamber to the casting chamber under the condition of $P_R > P_C$, thereby replacing and discharging the atmosphere in the mold in the casting chamber with inert gas and establishing a non-oxidizing atmosphere in the melting chamber and the casting chamber and drying the mold in an unheated state by dry inert gas evapotranspiration treatment, and a step of precision casting conducted by thereafter melting a fusible casting material and pouring it into the mold in the casting chamber, wherein the melting chamber volume $V_1 = T/\alpha \cdot V_0 \cdot 1/P_C$, and the casting chamber volume $V_2 = T \cdot V_R/\alpha(P - P_R)$, where

| | | |
|---|---|---|
| $V_1$ | Melting chamber volume | (l) |
| $V_2$ | Casting chamber volume | (l) |
| $V_0$ | Gas influx capability | (l/s) |
| T | Solidification time | (s) |
| $V_R$ | Gas leakage from mold | (l/s) |
| $P_R$ | Casting chamber pressure at time of arc discharge | (kg/cm² abs) |
| $P_C$ | Compressed gas pressure | (kg/cm² abs) |
| P | Casting chamber atmospheric discharge pressure | (kg/cm² abs) |
| $\alpha$ | Coefficient which is an experimentally determined numerical value defining the time, relative to the molten metal casting solidification time T, at which the interior of the melting chamber is increased to pressure $P_R$. | |

2. The method according to claim 1, wherein the melting chamber is maintained at positive pressure and the casting chamber is controlled to negative pressure from the system air discharge step to the completion of casting.

* * * * *